United States Patent [19]

Chang et al.

[11] Patent Number: 5,064,952

[45] Date of Patent: Nov. 12, 1991

[54] DERIVATIVES OF PORPHYRIN USEFUL IN PHOTODYNAMIC THERAPY

[75] Inventors: Chi-Kwong Chang, Brighton; Weishih Wu, East Lansing, both of Mich.

[73] Assignee: Board of Trustees, a Constitutional Corporation Operating Michigan State University, East Lansing, Mich.

[21] Appl. No.: 464,860

[22] Filed: Jan. 16, 1990

[51] Int. Cl.$^5$ .................. C07D 487/22; A61K 31/40
[52] U.S. Cl. ............................................. 540/145
[58] Field of Search ............... 514/185, 410; 540/145

[56] References Cited

U.S. PATENT DOCUMENTS

| | | |
|---|---|---|
| 4,485,806 | 12/1984 | Akers . |
| 4,500,507 | 2/1985 | Wang . |
| 4,512,762 | 4/1985 | Spears . |
| 4,577,636 | 4/1986 | Spears . |
| 4,649,151 | 3/1987 | Dougherty et al. . |
| 4,727,027 | 2/1988 | Wiesehahn et al. . |
| 4,748,120 | 5/1988 | Wiesehahn . |
| 4,753,958 | 6/1988 | Weinstein . |

FOREIGN PATENT DOCUMENTS 0220686 5/1987 European Pat. Off. .

OTHER PUBLICATIONS

Gregorie, Jr., et al, Ann. Surg., vol. 167, #6, 1968 pp. 820–828.
Diamond et al, Lancet, vol. 2, pp. 1175–1177, 1972.
Dougherty et al, Cancer Research, vol. 38, pp. 2628–2635, 1978.
Dougherty et al, Cancer: Principles & Practice of Oncology, pp. 1836–1844, 1980 Devita, Jr., et al. eds.
Mew et al, Journal Immunology, vol. 130, #3, pp. 1473–1477, 1983.
Mew et al, Cancer Research, vol. 45, pp. 4380–4386, 1985.
Oseroff et al, Proc. Natl. Acad. Sci., vol. 83, pp. 8744–8748, 1986.
Arasasingham et al, Heteocycles, vol. 27, pp. 2111–2118, 1988.
Dougherty et al, "The Science of Photomedicine", Regan E. Parish Publishers, 1982, pp. 626–638.
Dougherty et al, "Porphyrin Localization and Treatment of Tumors", pp. 301–314, 1984.
Kessel et al, Photochemistry & Photobiology, vol. 46, 45, pp. 563–568 1987.

*Primary Examiner*—Jose G. Dees
*Assistant Examiner*—Deborah D. Carr
*Attorney, Agent, or Firm*—Irell & Manella

[57] ABSTRACT

Compounds which are long wavelength-absorbing derivatives of porphyrinone nuclei are described which are useful in photodynamic therapy and related technologies. These compounds contain the porphyrin nucleus beta-substituted with alkyl and/or omega-carboxyalkyl substituents wherein the ring system contains at least one exocyclic double bond in which the exocyclic participant is selected from the group consisting of =S, =CR'$_2$, and NR''.

10 Claims, 17 Drawing Sheets

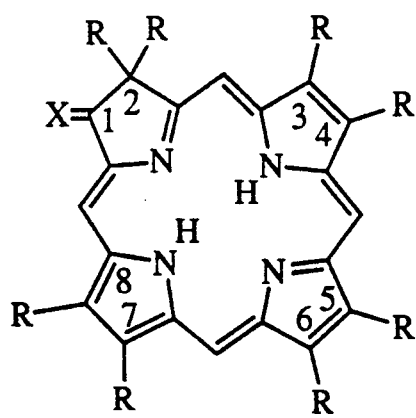
1
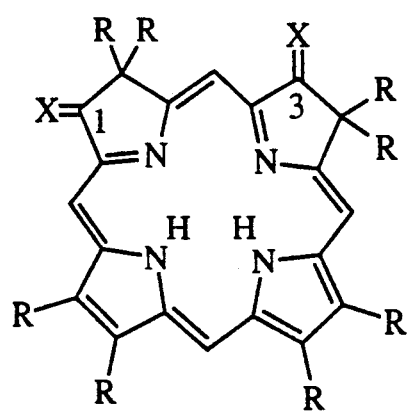
2
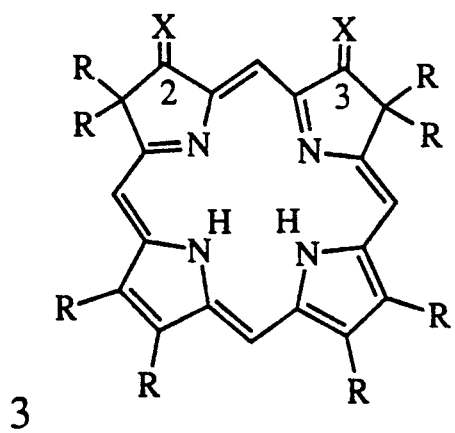
3
Figure 1-1

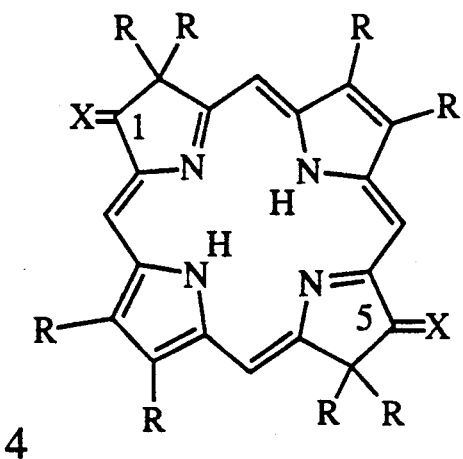
4
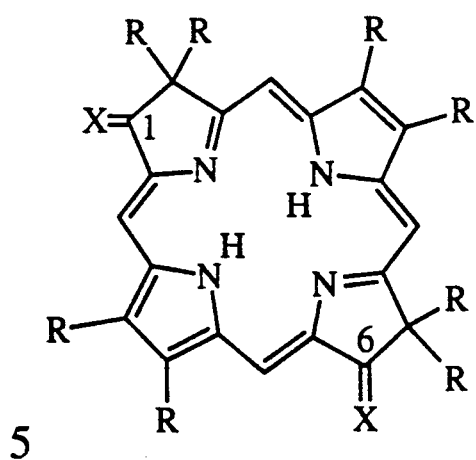
5
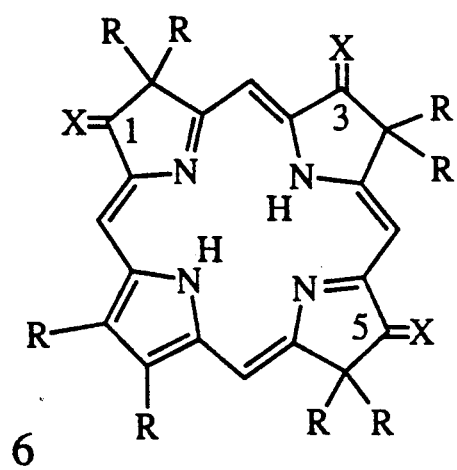
6
Figure 1-2

DERIVATIVES OF PORPHYRIN USEFUL IN PHOTODYNAMIC THERAPY

TECHNICAL FIELD

The invention relates to compounds with desirable absorption maxima for use in photodynamic therapy. More specifically, it concerns compounds which comprise a beta-substituted porphyrin nucleus which contains one, two, or three exocyclic double bonds to carbon, nitrogen or sulfur. These compounds show absorption wavelengths that are highly desirable for the use of these compounds in photodynamic therapy and related methodologies.

BACKGROUND ART

The use of porphyrin-type photosensitizers for the selective destruction of, for example, cancer cells in animal subjects has been known for several decades. The initial work utilized a mixture of porphyrins prepared from hematoporphyrin by treatment of this starting material with a mixture of sulfuric and acetic acids to result in a composition known specifically as hematoporphyrin derivative (HPD). (See, for example, "Porphyrin Photosensitization" Kessel, D., et al., eds. (1983) Plenum Press.)

HPD and related porphyrin-type photosensitizers appear to localize in malignant cells at the expense of normal tissues. The cells in which the HPD has been accumulated can then be irradiated using light of an appropriate wavelength absorbed by the HPD. When irradiated, the HPD and related photosensitizers have two properties which make them useful. First, when irradiated with the appropriate wavelength, the compound is capable of fluorescence and can thus be used to detect cells in which it is accumulated (see, for example, Kessel, D., et al., (supra); Gregory, H. B., Jr., et al., *Ann Surg* (1968) 167:827–829). Second, HPD and its relatives discussed below are useful in therapeutic methods because when irradiated with visible light, a cytotoxic effect on the cells in which they are localized is exerted (see, for example, Diamond, I., et al., *Lancet* (1972) 2:1175–1177; Dougherty, T. J., et al., *Cancer Research* (1978) 38:2628–2635; Dougherty, T. J., et al., "The Science of Photomedicine" (1982) J. D. Regan and J. A. Parrish eds.; Dougherty, T. J., et al., *Cancer: Principles and Practices of Oncology* (1982) B. T. DeVita Jr., et al., eds.) An improved photosensitizer which is prepared from HPD by adjustment of pH to cause aggregation and recovery of the aggregate is disclosed in U.S. Pat. No. 4,649,151, incorporated herein by reference. The "purified" form of the mixture is called dihematoporphyrin ether (DHE) in the patent and is marketed under the trademark Photofrin® II. This has been used, as described in U.S. Pat. No. 4,649,151 in a manner completely analogous to HPD.

Other porphyrin-type photosensitizers have also been reported, including various chlorophyll derivatives derived from both bacteria and higher plants. A group of compounds of particular interest is that described as green porphyrins (Gp) in U.S. Pat. No. 4,883,790, also incorporated herein by reference. These compounds are so designated because they absorb light at longer wavelengths than that absorbed by hematoporphyrin derivative or its related compounds, and therefore these porphyrins appear green in white light. The green porphyrins are derived from protoporphyrin IX by a reaction with a single acetylenic dienophile in a Diels-Alder reaction, and optional subsequent rearrangement and/or reduction. A subset of green porphyrins, designated herein benzoporphyrin derivatives (BPD) are particularly useful among this group.

All of the porphyrin-type photosensitizing compounds described in the literature are generally useful in the same manner as hematoporphyrin derivative as set forth in the above-cited art. In addition, however, to in vivo therapeutic and diagnostic protocols for tumors, as described above, these compounds can be used in other in vivo and in vitro applications. For example, these photosensitizers are useful in the detection of atherosclerotic plaques as described in U.S. Pat. Nos. 4,512,762 and 4,577,636. U.S. Pat. Nos. 4,500,507 and 4,485,806 describe the use of radiolabeled porphyrin compounds, including HPD, for tumor imaging. U.S. Pat. No. 4,753,958 describes the use of topical applications of porphyrin sensitizers for diagnosis and treatment of skin diseases. U.S. Pat. No. 4,748,120 describes the use of photosensitizers in the treatment of whole blood or blood components to rid them of infectious agents. Photochemical decontamination treatment of blood and components is also described in U.S. Pat. No. 4,727,027 where the photosensitizer is furocoumarin and its derivatives, rather than porphyrin-type materials. In addition, viruses are inactivated in therapeutic protein compositions in vitro as disclosed in U.S. Pat. No. 4,268,947.

For the administration of the porphyrin related photosensitizers in in vivo applications, various pharmaceutical compositions have been suggested. In one approach, the photosensitizing drug was coupled to antibodies which putatively enhance the ability of the drug to localize in the desired target cell. For instance, HPD was coupled to antibodies directed to the murine myosarcoma cell line M1 as described by Mew, D., et al., *J Immunol* (1983) 130:1473–1477. HPD was also conjugated to CAMAL-1 antibodies which are directed to a human leukemia antigen (Mew, D., et al., *Cancer Research* (1985) 45:4380–4386). The conjugation of chlorin $e_6$ to anti T-cell monoclonal antibody was described by Oseroff, A. R., et al., *Proc Natl Acad Sci USA* (1986) 83:8744–8748.

In a dissertation submitted in 1987, Sotiriou, C., described the synthesis of thiones derived from octaethyl porphyrin using Lawesson's reagent. Compounds containing one, two, and three thione substituents were obtained. Some were further reduced to the thiols. Spectra of the compounds were determined, but no utility was suggested. A paper by Arassingham, R. D., et al., *Heterocycles* (1988) 27:2111–2118, is an additional report of the synthesis of these thiones of octaethyl porphyrin. Again, although spectra were provided, no utility was disclosed.

Although many porphyrin-type compounds and multi-ring systems have been suggested for use in photodynamic therapy and related methodologies, not all have satisfactory properties for all clinical or even laboratory situations, and many absorb light at wavelengths which are also absorbed by tissue. The presence of the latter problem results in the need for elevated dosages, which only aggravates the problems of side effects and undesirable reactions unrelated to the ability of the photosensitizers to destroy neoplastic or other unwanted tissue.

DISCLOSURE OF THE INVENTION

The invention provides a class of porphyrin ring compounds which have particularly favorable absorption spectra for use of these compounds in photodynamic therapy, and which adds these compounds to the repertoire of possible drugs useful in the same general manner as HPD, DHE, BPD, and other related compounds. The compounds of the invention are beta-substituted porphyrin derivatives which further contain 1-3 exocyclic double bonds linking a ring carbon to carbon, nitrogen or sulfur. More specifically, the exocyclic substituent is selected from the group consisting of $=CR'_2$; $=S$; and $NR''$.

The compounds of the invention are beta-substituted porphyrin nuclei, containing or not containing coordinated metal ion, wherein at least one of the pyrrole rings is of the general form:

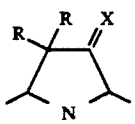

wherein X is selected from the group set forth above. The remainder of the ring is conjugated according to its position in the tetrapyrrole system.

FIG. 1 shows the structures of the compounds included within the invention. The R groups are the same or different and are selected from the group consisting of H, alkyl(1-6C), and omega-carboxyalkyl(1-6C) and the esters, amides, and salts thereof. The pattern of the R-substitution is relevant not only to the efficacy of the compounds, but to the ease with which they can be obtained and synthesized. R groups which occur in nature are therefore included within the compounds of the invention, since methods to convert the naturally occurring compounds to those containing at least one $=X$ substituent are known in the art. Also favored are compounds wherein all R groups are identical or wherein they show a regular pattern, as compounds of this type can readily be synthesized de novo. More complex patterns of arbitrary R groups can also be obtained, but generally the preparations of these result in mixtures which may then require separation.

Accordingly, in one aspect, the invention is directed to compounds of the formulas shown in FIG. 1 wherein X is selected from the group consisting of $=CR'_2$, $=S$, $=O$, and $NR''$, wherein each R' is independently H, cyano, alkyl(1-6C), or omega-carboxyalkyl(1-6C) or the esters, amides or salts thereof, or aryl; each R'' is OH, CN, alkyl(1-6C), or omega-carboxyalkyl(1-6C) or the esters, amides or salts thereof; and wherein each R is independently H, alkyl(1-6C) or omega-carboxyalkyl(1-6C) or the esters, amides or salts thereof; with the proviso that if all R are ethyl, all $=X$ cannot be either $=O$ or $=S$, and with the further proviso that at least one $=X$ must be other than $=O$.

In other aspects, the invention is directed to pharmaceutical compositions wherein the active ingredient is a porphyrin-derived compound described herein, and to methods to conduct photodynamic therapy and diagnosis, or to treat products to rid them of infective agents using the compounds and compositions of the invention. The invention is also directed to methods to synthesize certain embodiments of the invention compounds.

BRIEF DESCRIPTION OF THE DRAWINGS

FIG. 1-1 thruway 1-6 shows the formulas for the six prototype nuclei for the compounds of the invention.

MODES OF CARRYING OUT THE INVENTION

Figure 2A:
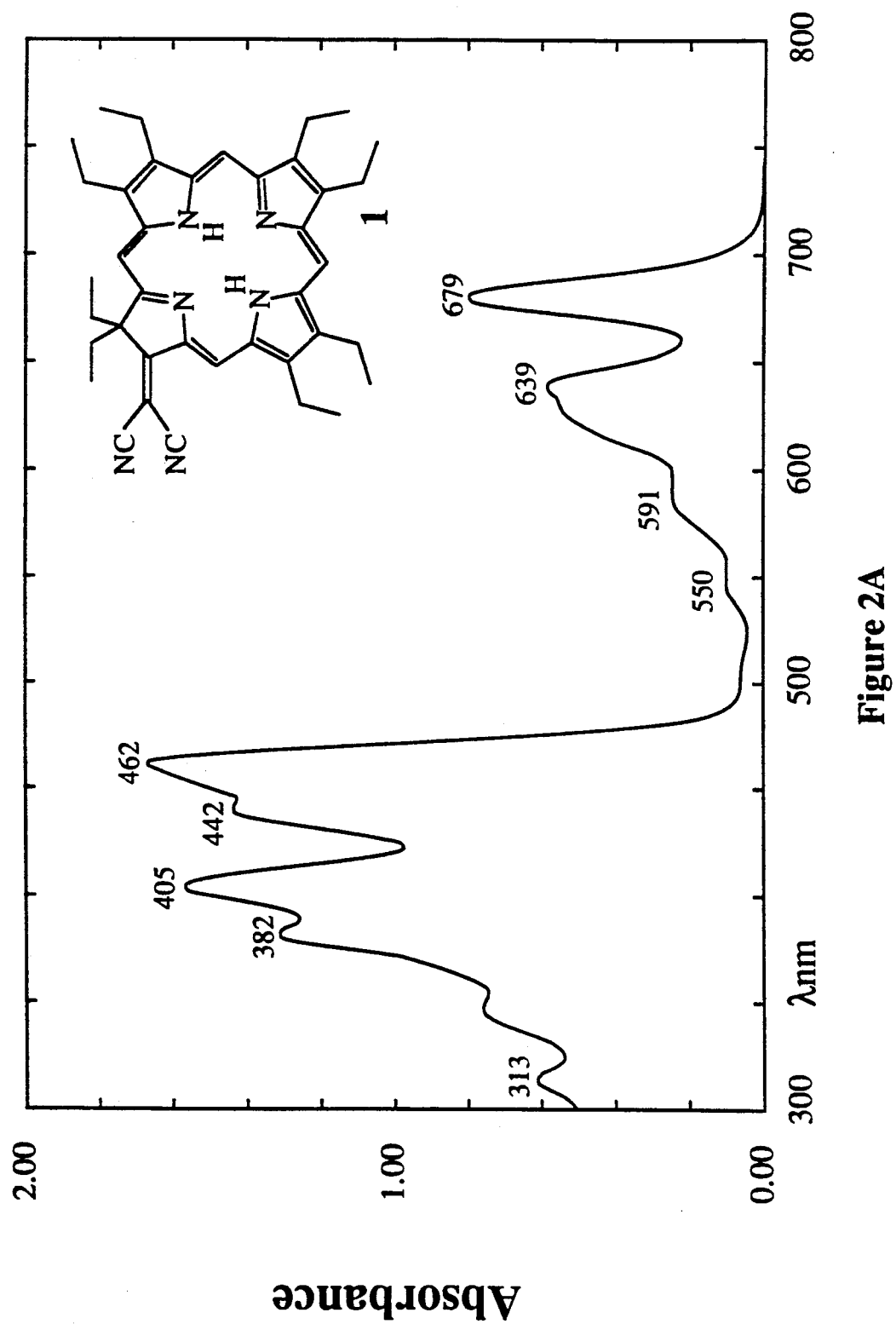
FIG. 2A thruway 20 shows the absorption spectra of various compounds of the invention and indicates high absorption in the range 680 nm or higher.

The invention provides compounds which are suitable for photodynamic therapy or other related applications already known for other porphyrin photosensitizers. However, these compounds are advantageous in having particularly long wavelength absorption spectra.

The Photosensitizers of the Invention

FIG. 1 shows the formulas for the six prototype nuclei of the invention compounds. Although the nuclei are shown in the form wherein the cations are $H^+$, it is understood that the compounds of the invention also include embodiments wherein the hydrogen ions are replaced by other suitable cations, such as $Cu^{+2}$, $Zn^{+2}$, $Sn^{+4}$, $Al^{+3}$ or any suitable metal ion. As explained below, the metal ions may include those which are radioisotopes and are hence useful as labels.

The compounds of formula 1 contain only one exocyclic $=X$. Those in formulas 2 and 3 contain two such substituents in the A and B rings; the compounds of formulas 2 and 3 are isomers different only in the positions within the A and B rings of the exocyclic double bond. In these embodiments, the preferred forms include those in which one $=X$ is $=O$ and the other is selected from the group set forth above, in particular, wherein R' is H, or wherein both $=X$ are selected from this group and are identical.

The situation is similar with respect to the compounds of formulas 4 and 5 which contain these substituents in the A and C rings.

In the compound of formula 6, containing three exocyclic $=X$, it is preferred that one of the substituents is $=O$ and the other two are identical; two are $=O$ and the other is selected from the defined group; or all three $=X$ are identical and selected from the defined group.

With respect to R', each R' is independently selected and is H, cyano, alkyl(1-6) or omega-carboxyalkyl (1-6C) or the esters, amides or salts thereof, or is aryl. Alkyl has its conventional meaning and can be a straight or branched chain hydrocarbyl residue such as methyl, isopropyl, n-hexyl, and the like. The carboxy group of the omega-carboxy alkyl can be present as the free acid or as the ester, amide or salt. The esters are preferably alkyl esters (1-6C). Amides may be primary, secondary, or tertiary amides, also of alkyl(1-6C). Salts are formed with a suitable pharmaceutically acceptable cation, typically sodium, potassium, calcium, ammonium, and the like. Organic cations may also be used in salt formation. Aryl is phenyl or an aromatic monocyclic heterocyclic substituent. In the most preferred embodiments, both R' are H.

R'' is OH, cyano, alkyl(1-6C) or omega-carboxyalkyl (1-6C) or the esters, amides and salts thereof (all defined as above). In the most preferred embodiments R'' is CN.

With respect to R, embodiments wherein all R are identical or wherein all R provide a regular alternating pattern are preferred. R is selected from the group consisting of H, alkyl (1-6C), and omega-carboxy alkyl(1-6C), in particular, carboxy ethyl, as this is the native substituent. In this instance, preferred embodiments include those wherein the arrangement of R groups is that provided in naturally occurring porphyrins.

Figure 2B:
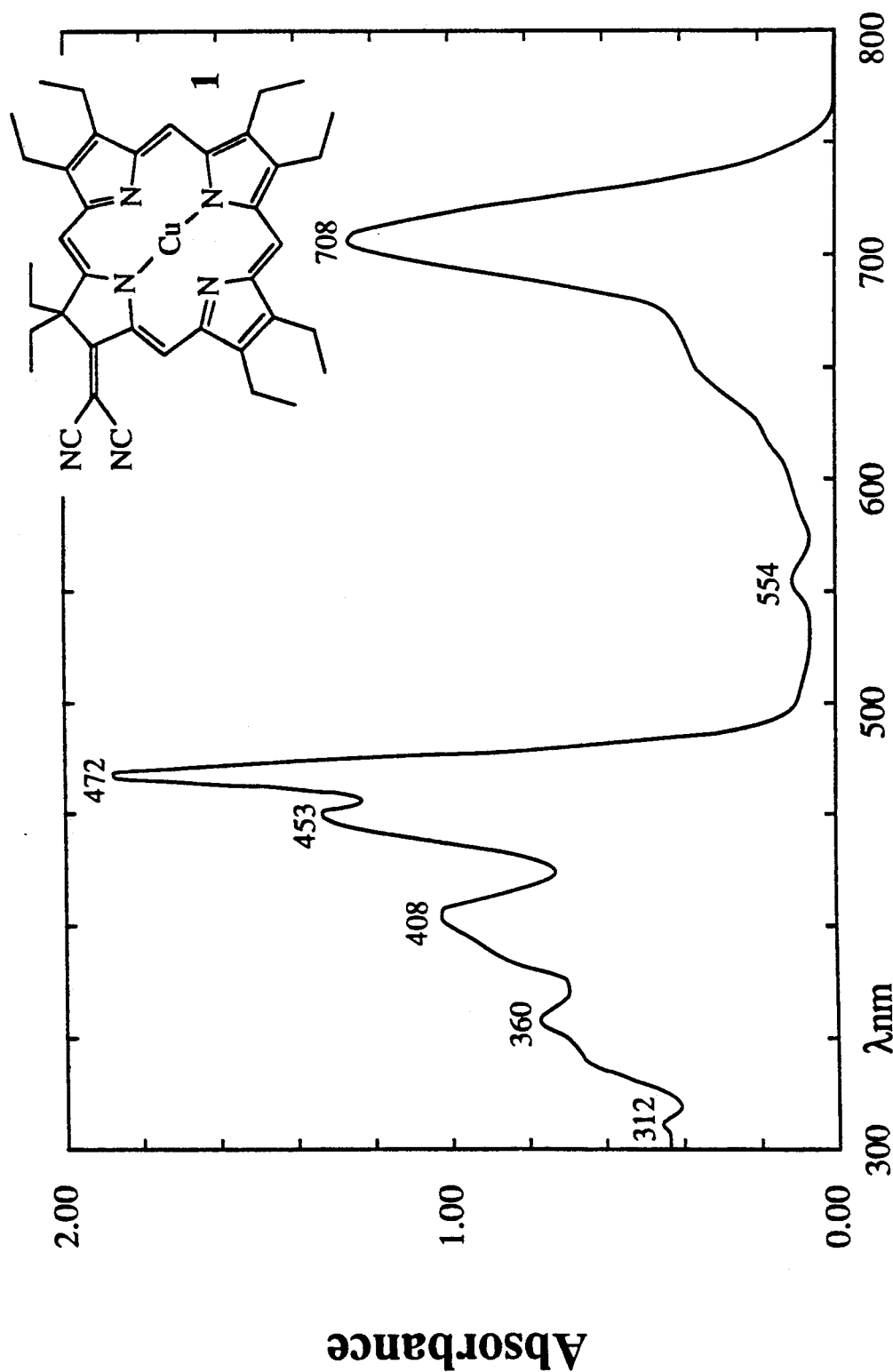
Figure 2C:
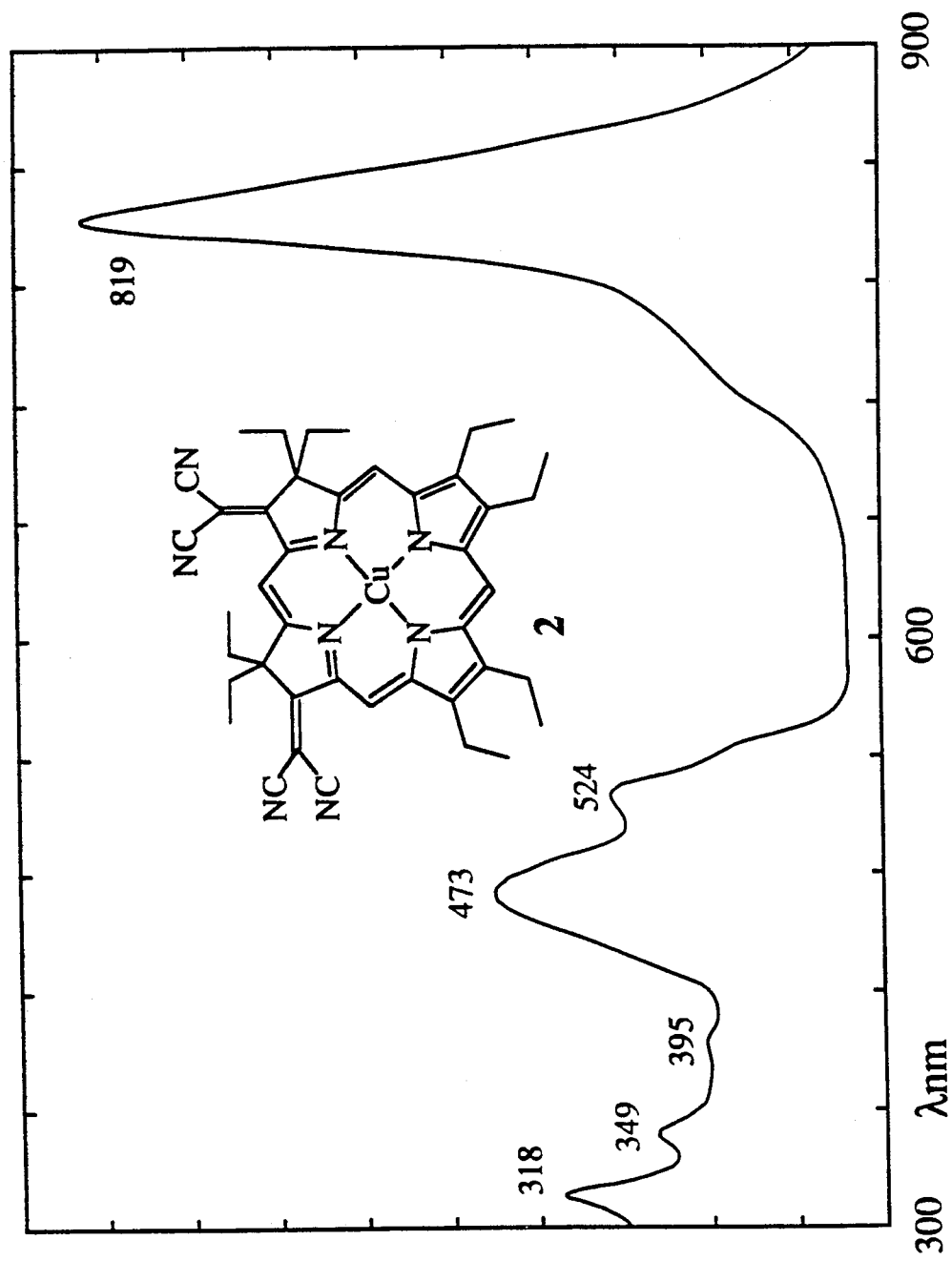
Figure 2D:
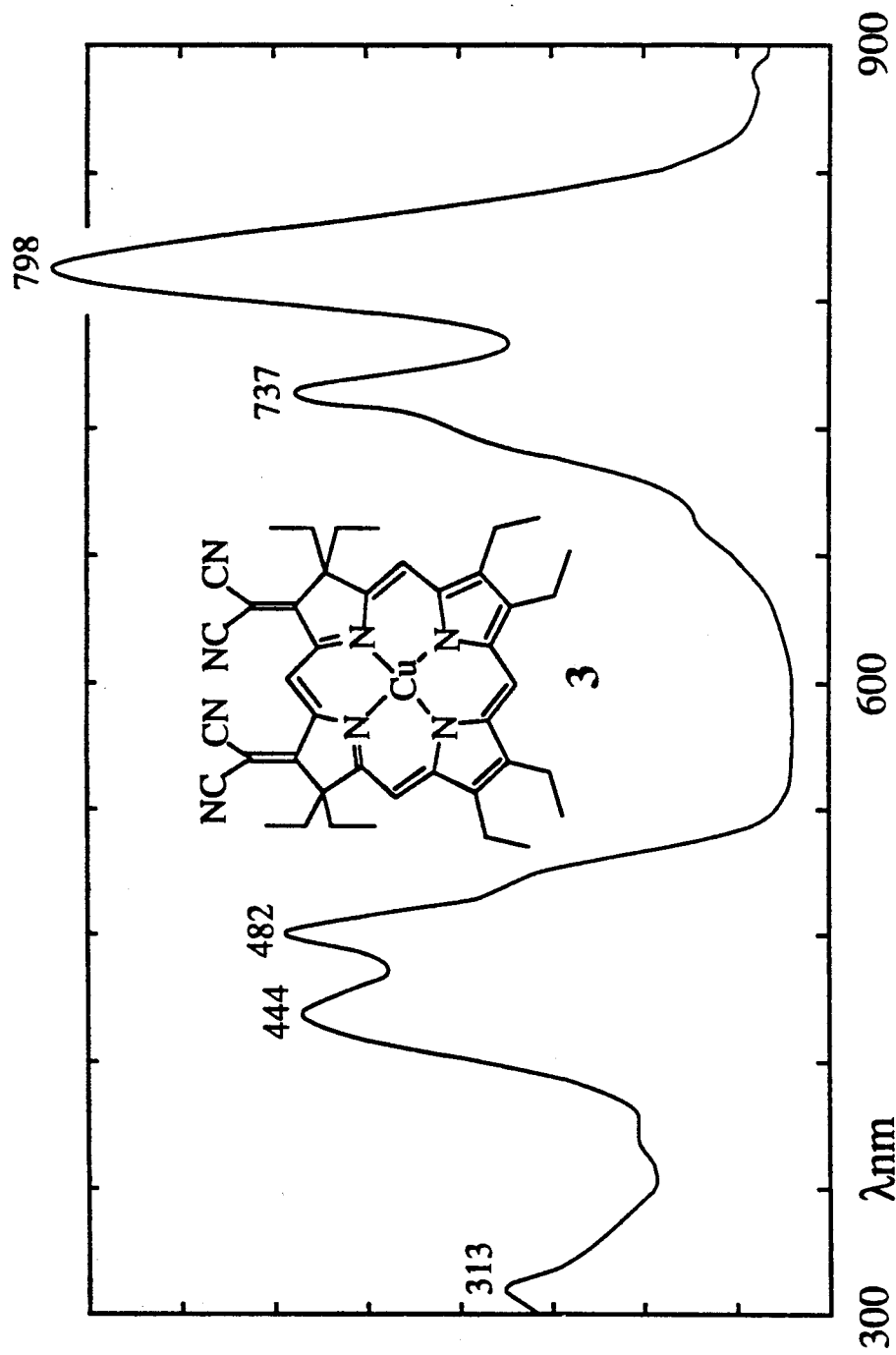
Figure 2E:
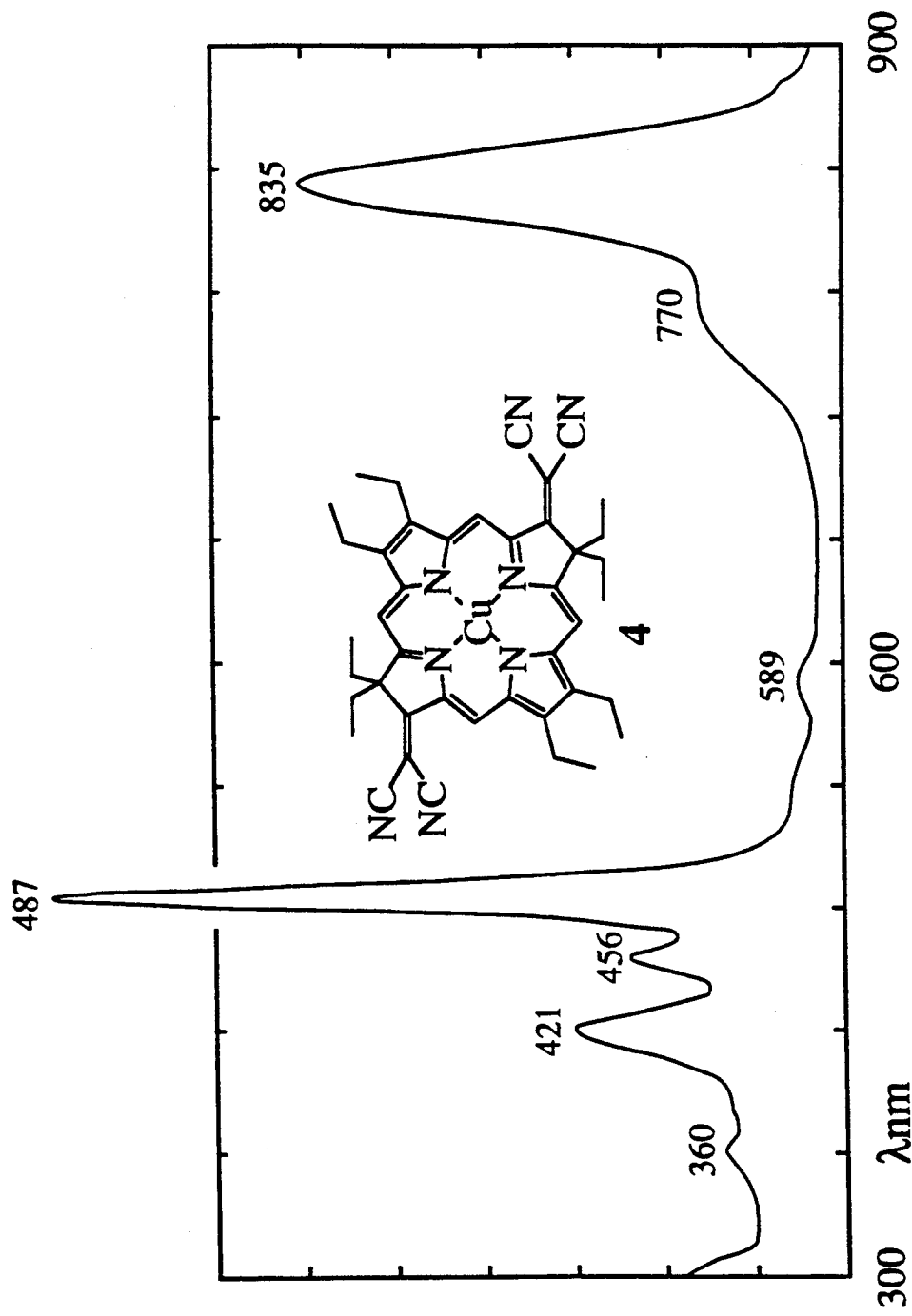
Figure 2F:
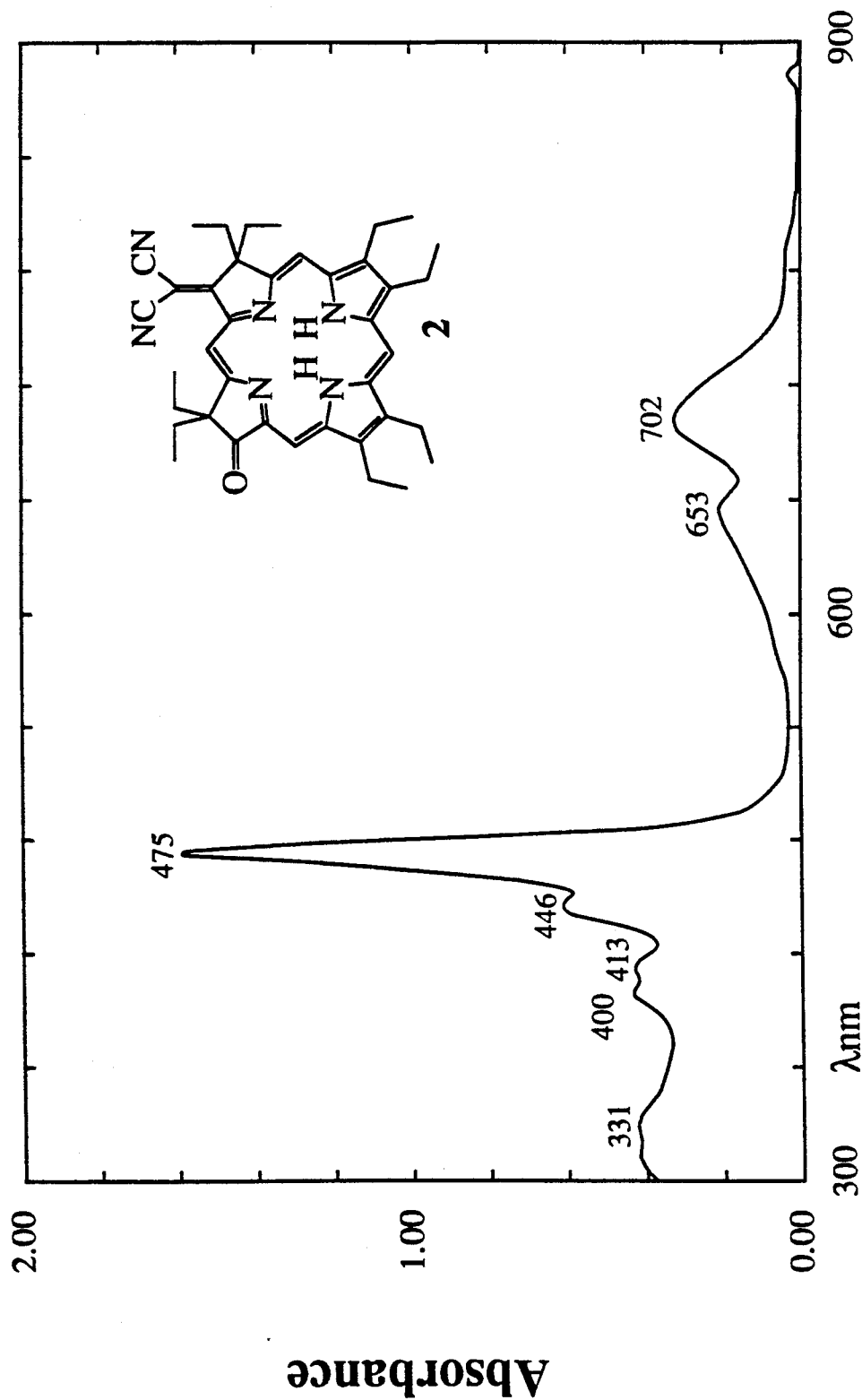
Figure 2G:
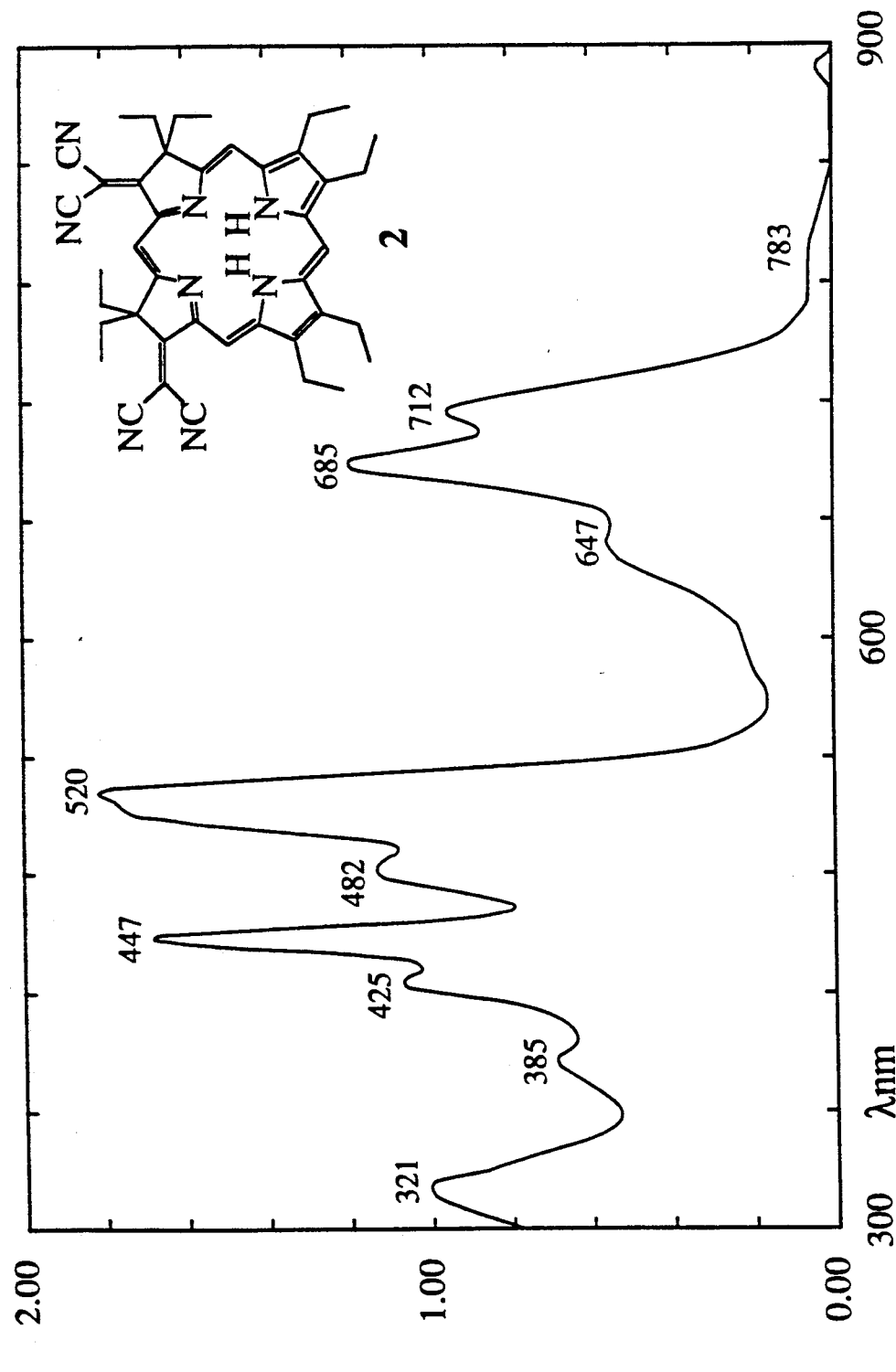
Figure 2H:
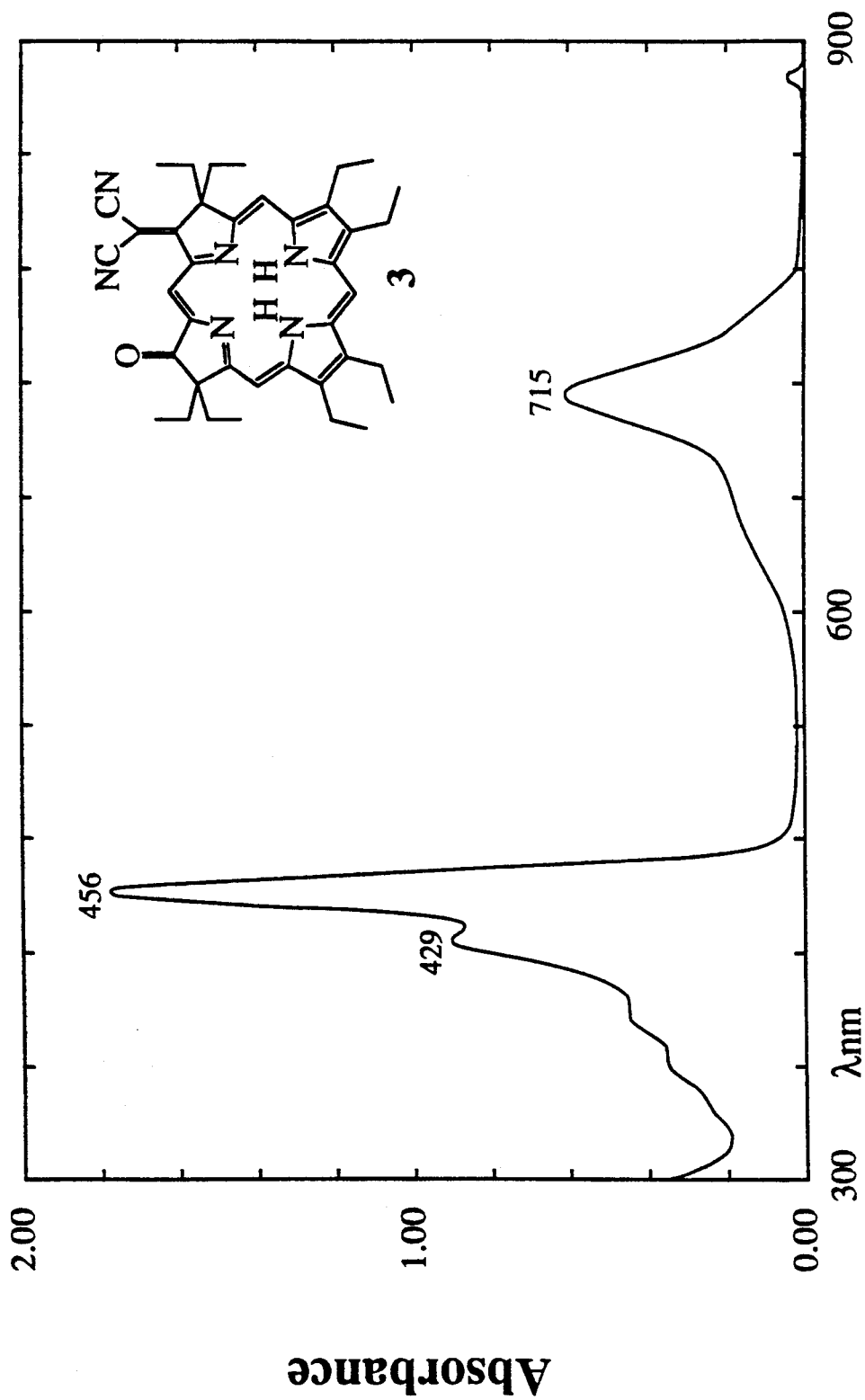
Figure 2I:
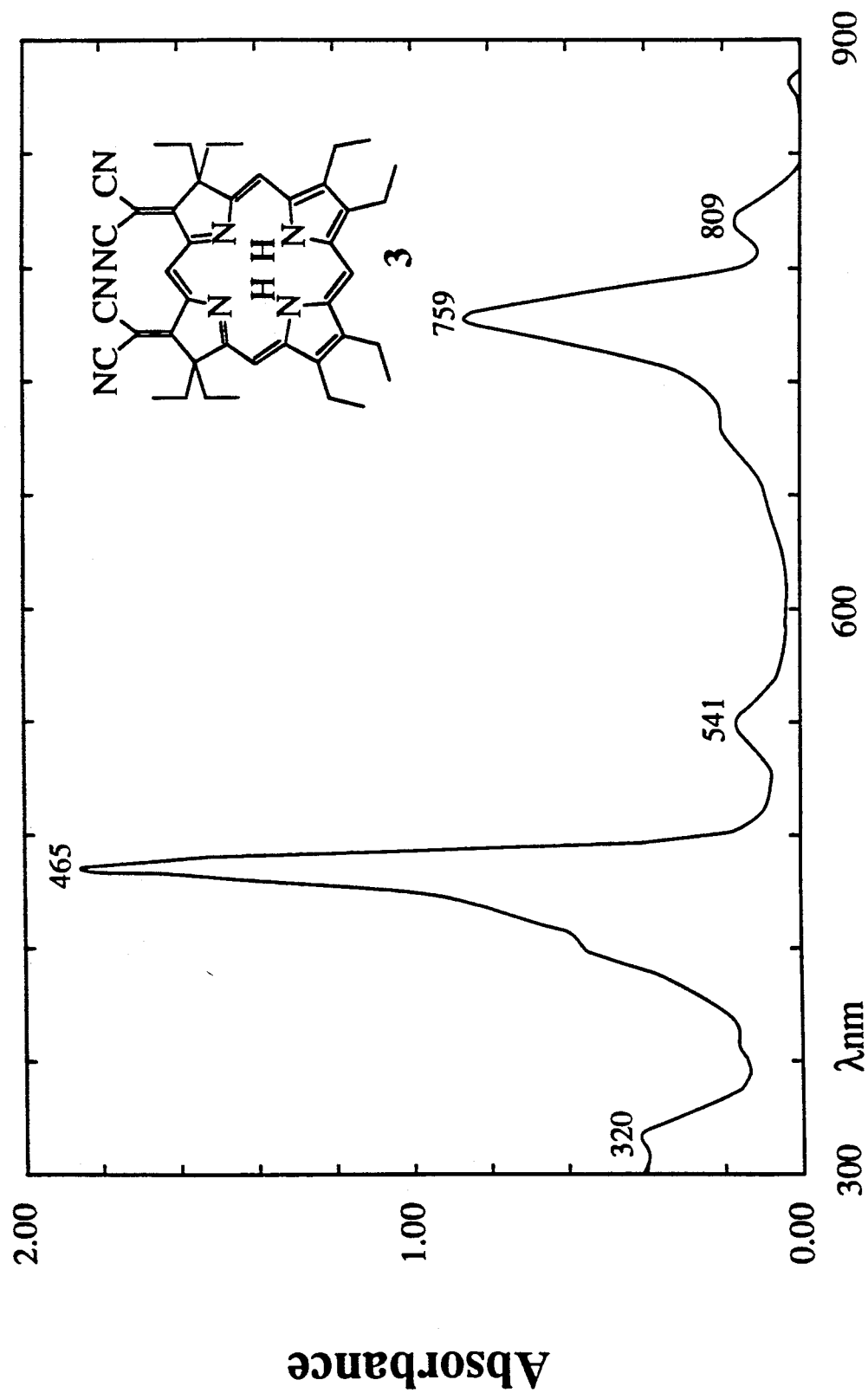
Figure 2J:
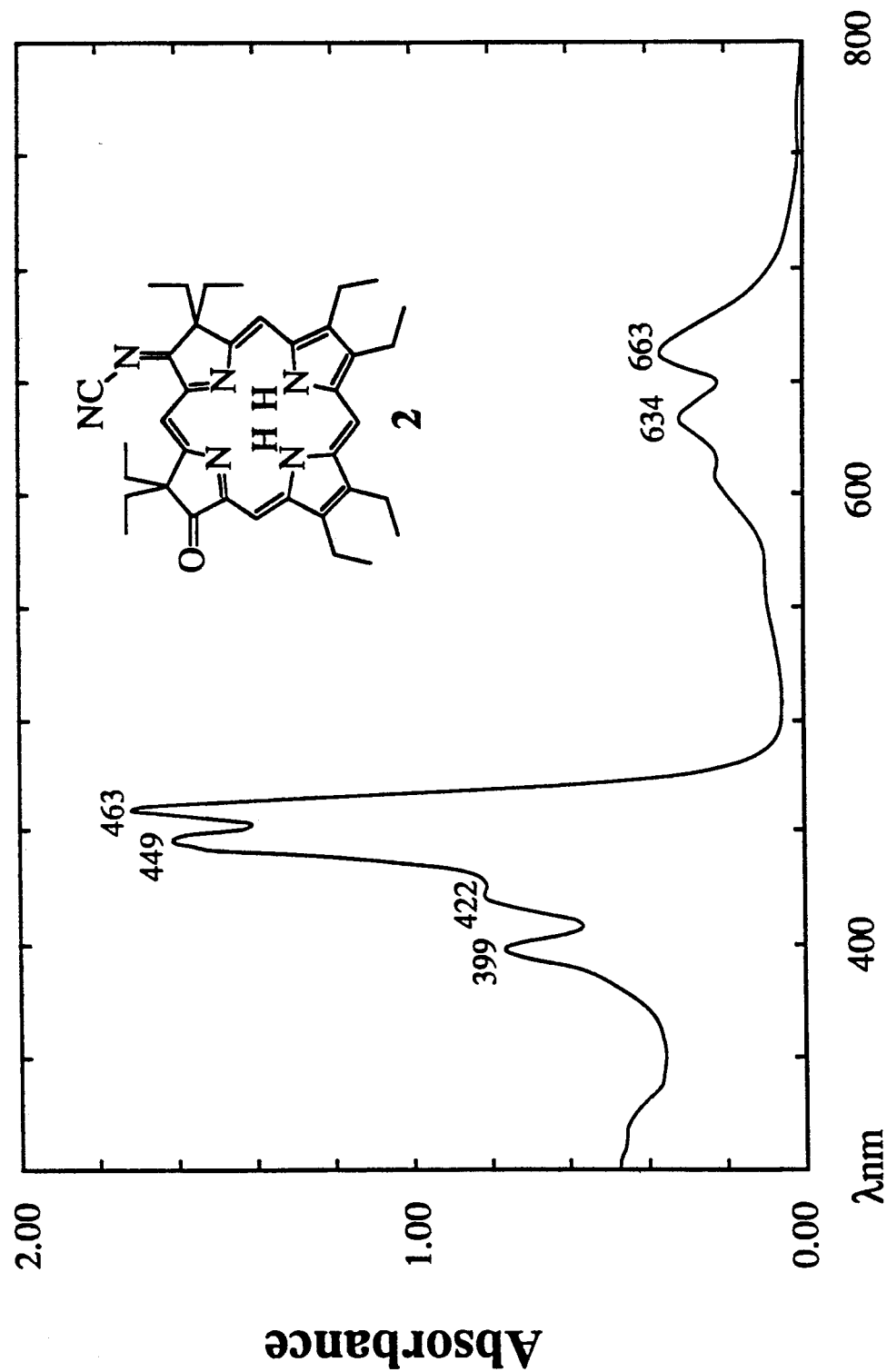
Figure 2K:
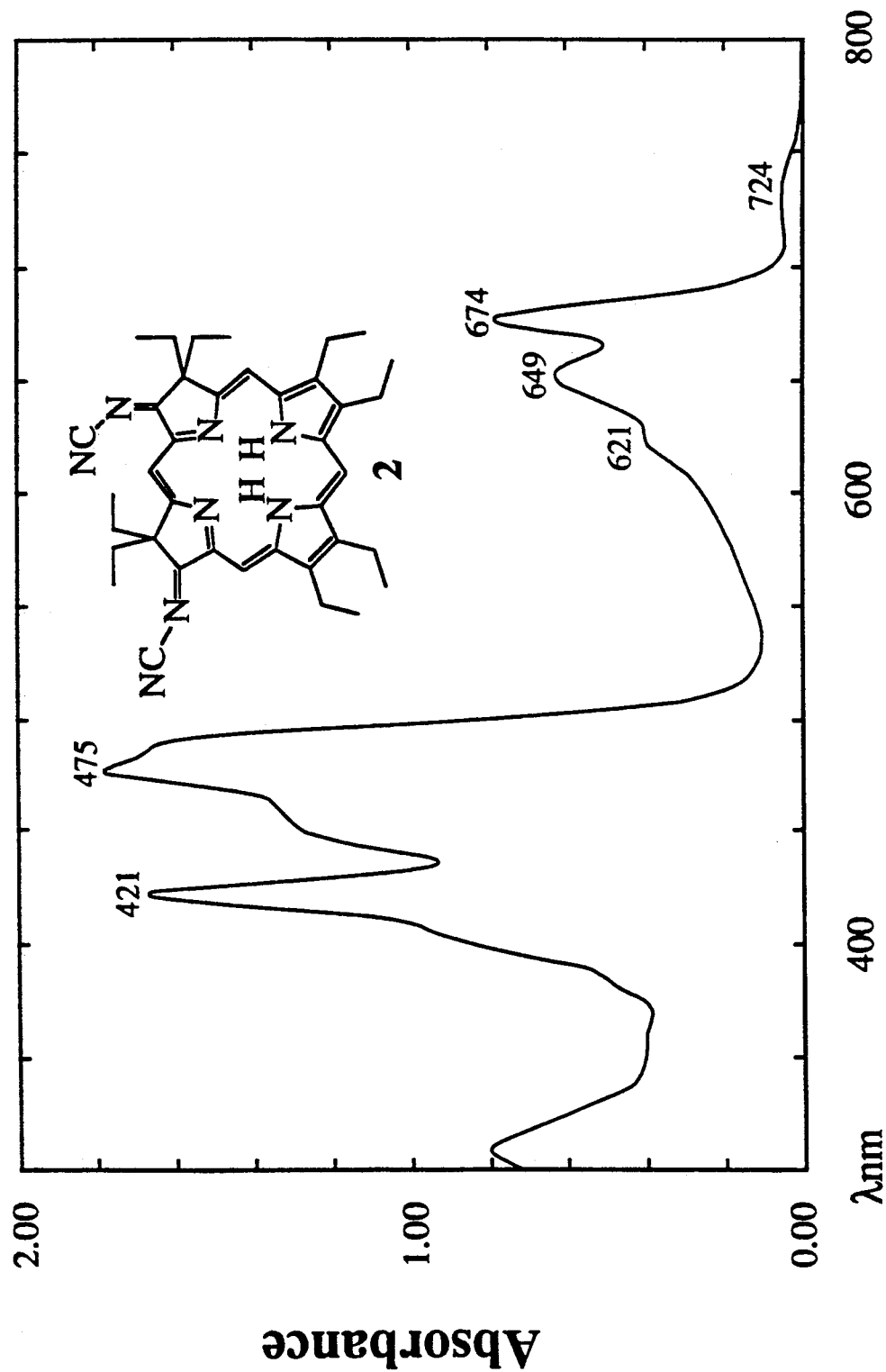
Figure 2L:
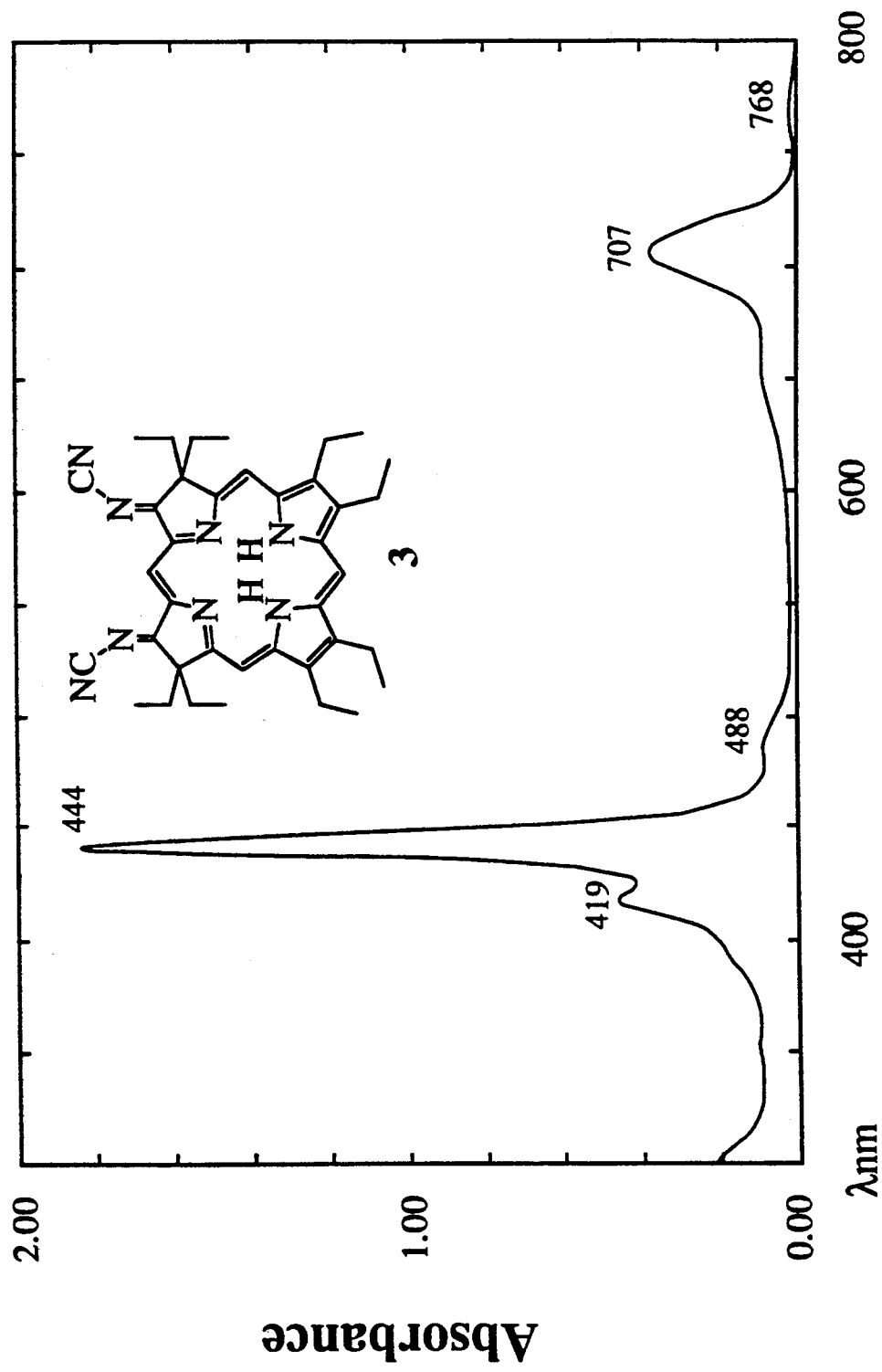
Figure 2M:
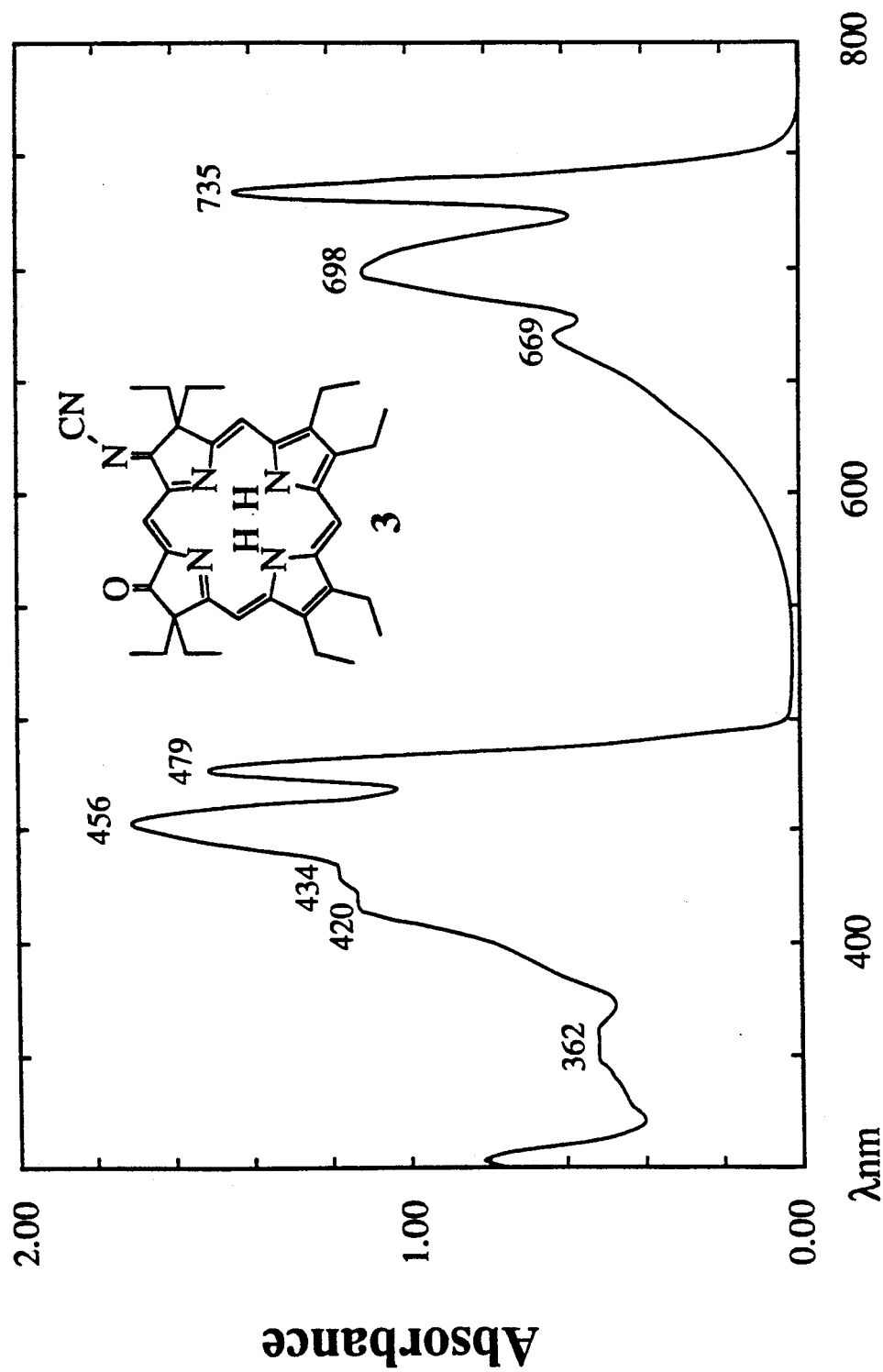
Figure 2N:
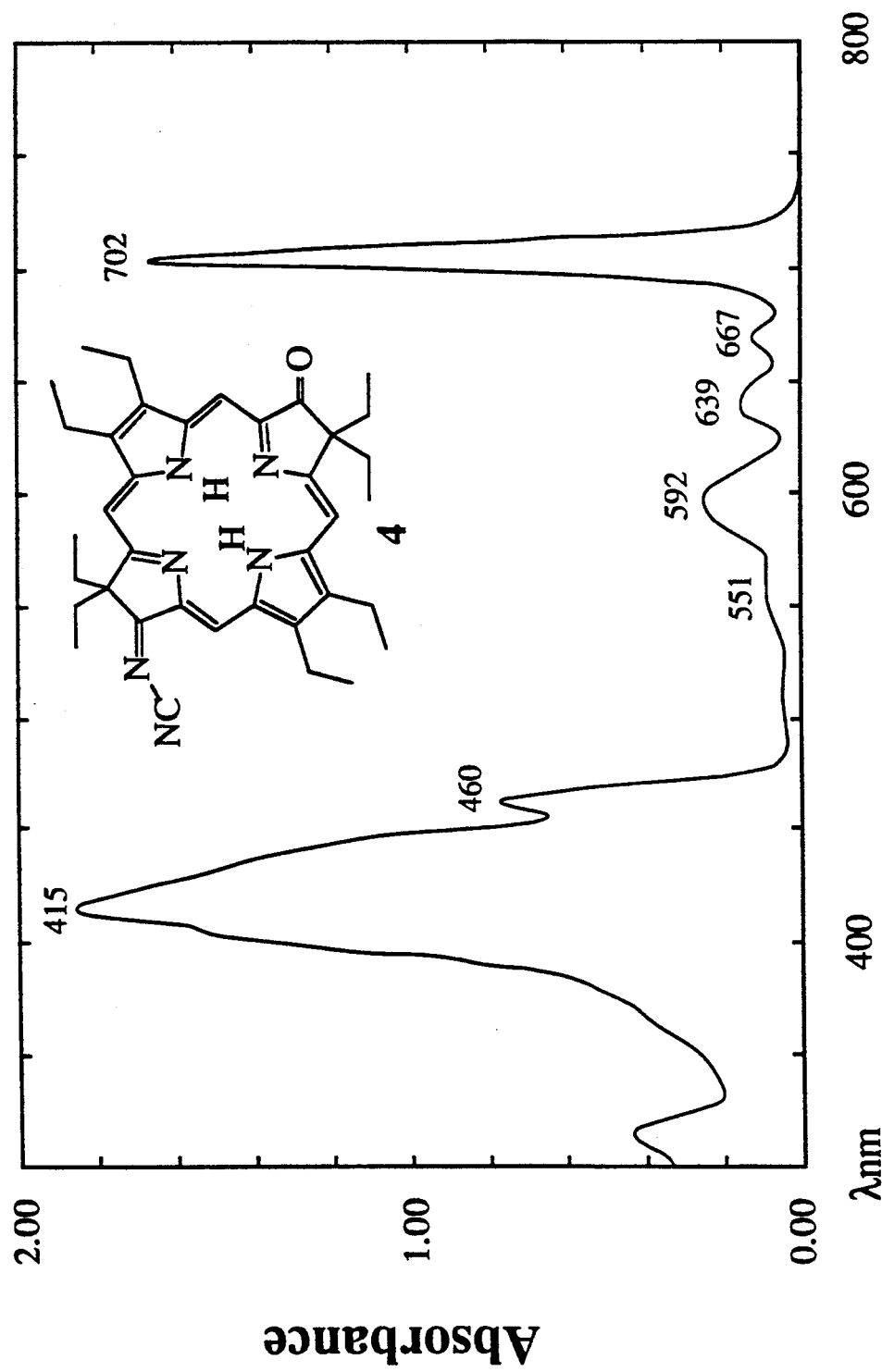
Figure 20:
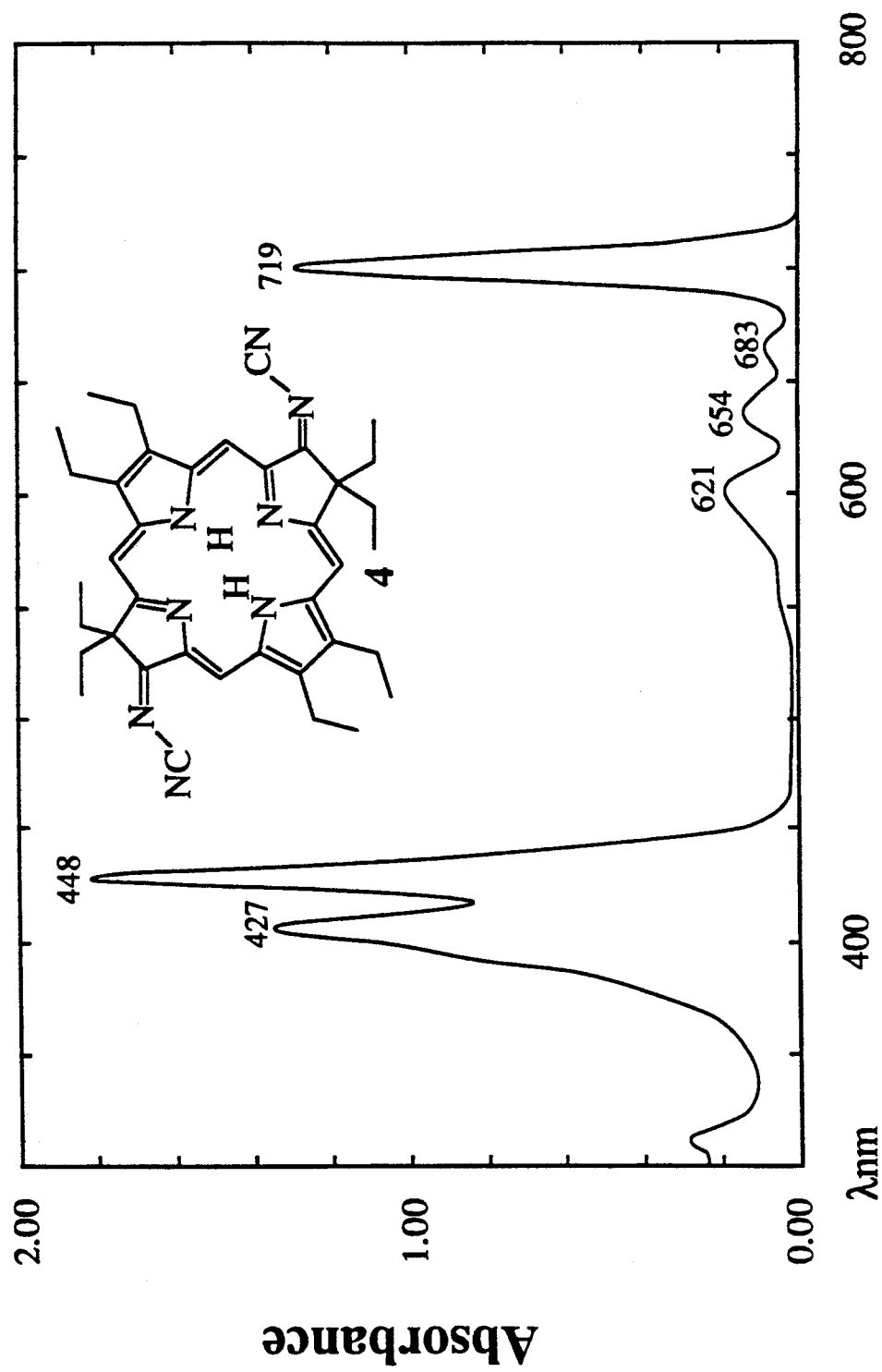

Particularly preferred embodiments of the compounds of the invention along with their spectra are shown in FIG. 2. The formula to which these compounds correspond is shown under the structure in each case. The spectra show significant absorption at the >680 nm region.

Preparation of the Photosensitizers

In general, the compounds of the invention are prepared from the corresponding forms wherein all =X are =O. These compounds are available in the art or are readily prepared from known compounds. For example, mono and diketo derivatives of protoporphyrin, some of which retain the native substituents in alternate positions, are described in Wu, W. et al., *J Am Chem Soc* (1987) 104:3149-3150. Suitable derivatives of sirohydrochlorin are described by Chang, C. K.; *Biochemistry* (1980) 19:1971-1976. Synthesis of mesoporphyrindiones is described in Chang, C. K., et al., *J Org Chem* (1986) 51:2134-2137. All of these disclosures are incorporated herein by reference.

To convert the keto group to the thione, the oxo analog is treated with 2,4-bis-(p-methoxyphenyl)-1,3-dithia-2,4-diphosphetane-2,4-disulfide (Lawesson's reagent).

To obtain the corresponding -N-R' derivatives, such as N-cyanoiminyl, the method of Aumuller, A., *Angew Chem Int Ed Engl* (1984) 23:447-448, may be used. This method employs bis-(trimethylsilyl)-carbodiimide together with titanium tetrachloride. The reaction is conducted in an inert solvent such as methylene chloride at approximately room temperature and takes several hours.

For synthesis of the dicyanomethylenyl compounds, the method of Aumuller, A., et al., *Liebigs Ann Chem* (1984), 618-621, is used. This is a one-step reaction utilizing titanium chloride, pyridine, and malononitrile. In general, the substrate containing the keto group is treated with approximately 3 equivalents of malononitrile in, for example, refluxing chloroform containing 2 equivalents of titanium tetrachloride and an excess of pyridine for about 30 minutes. If the copper-containing porphyrinone form is used, copper can be removed by addition of $H_2S$.

Other embodiments wherein =X is =$CR'_2$ are prepared by alkylation of the keto groups by alkyllithium followed by dehydration with $MsCl-Et_3N$ (Chang, *Biochemistry* (1980) 19:1971-1976), or using a Wittig reagent (Sotiriou, C., Dissertation, Michigan State University, East Lansing, Mich. (1987), pp. 92-113). In the Wittig reaction, the substrate ketone is treated with excess ylide in THF at room temperature for about 20 hours. The product is worked up using standard procedures.

Additional Components of the Invention Compositions

In addition to the compounds of the invention, certain additional components may be included in their pharmaceutical compositions. These include targeting components, additional label, and other functionalities which may be useful in the applications herein.

For example, an immunoglobulin or portion thereof or a ligand specific for receptor can be used as a target specific component. The immunoglobulin can be polyclonal or monoclonal antibody and may comprise whole antibodies or immunologically reactive fragments of these antibodies such as $F(ab')_2$, Fab, or Fab' fragments. Use of such immunologically reactive fragments as substitutes for whole antibodies is well known in the art. See, for example, Spiegelberg, H. L., in "Immunoassays in the Clinical Laboratory" (1978) 3:1-23.

The ligand specific for receptor will be a moiety which binds a receptor at cell surfaces, and thus contains contours and charge patterns which are complementary to those of the receptor. A variety of cell types have specific receptors designed to bind hormones, growth factors, or neurotransmitters, and these ligands specific for receptor are included as well as synthetic materials which bind specifically to a receptor. Examples of such ligands include the steroid hormones, such as progesterone, estrogens, androgens, and the adrenal cortical hormones; growth factors, such as epidermal growth factor, nerve growth factor, fibroblast growth factor, and so forth; other protein hormones, such as human growth hormone, parathyroid hormone, and so forth; and neurotransmitters, such as acetylcholine, serotonin, and dopamine, as well as analogs of these substances which bind receptors.

The compounds of the invention may be further derivatized to a compound or ion which is a label. A wide variety of labeling moieties can be used, including radioisotopes, chromophores, and fluorescent labels. Radioisotope labeling in particular can be readily detected in vivo. Radioisotopes may be coupled by coordination as cations in the porphyrin system. Useful cations include technetium, gallium, and indium.

In general, the compounds can also be administered or used in in vitro methods when complexed to appropriate metal ions. As is generally understood in the art, the tetrapyrrole-type nucleus can be treated with an appropriate ion such as magnesium ion, zinc ion, stannic ion, and the like to obtain the metal complex. As stated above, the metal ion may also be a radiolabel. The nature and desirability of the inclusion of a metal ion in the tetrapyrrole-type nucleus depends on the specific application for which the compound is intended. When the inclusion of a metal ion is desired, the desired metal ion can be inserted using the appropriate metal salts under known conditions. For example, zinc ion can be introduced by treating the compound with zinc acetate in a methylene chloride:methanol solvent mixture.

Administration and Use

The compounds of the invention are thus useful in general, in the manner known in the art for hematoporphyrin derivative and for DHE. These materials are useful in sensitizing neoplastic cells or other abnormal tissue to destruction by irradiation using visible light—upon photoactivation, the photosensitizer has no direct effect, nor it is entered into any biological event; however the energy of photoactivation is believed to be transferred to endogenous oxygen to convert it to singlet oxygen. This singlet oxygen is thought to be responsible for the cytotoxic effect. In addition, the photoactivated forms of porphyrin fluorescence which fluoresce can aid in localizing tumors or other sites to which the conjugates home.

Typical indications, known in the art, include destruction of tumor tissue in solid tumors, dissolution of plaques in blood vessels (see, e.g., U.S. Pat. No. 4,512,762); treatment of topical conditions such as acne, athlete's foot, warts, papilloma, and psoriasis and treatment of biological products (such as blood for transfusion) for infectious agents, since the presence of a membrane in such agents promotes the accumulation of the drug.

The compounds of the invention are formulated into final pharmaceutical compositions for administration to the subject or applied to an in vitro target using techniques known in the art generally. A summary of such pharmaceutical compositions may be found, for example, in *Remington's Pharmaceutical Sciences*, Mack Publishing Co., Easton, Pa., latest edition.

The compounds can be used in the systemic treatment of target tissues, cells and viruses, including tumors and neoplastics such as bronchial, cervical, esophageal or colon cancer and for the diagnosis of same. They can be administered systemically, in particular by injection, or can be used topically. They can be used singly or as components of mixtures.

Injection may be intravenous, subcutaneous, intramuscular, or even intraperitoneal. Injectables can be prepared in conventional forms, either as liquid solutions or suspensions, solid form suitable for solution or suspension in liquid prior to injection, or as emulsions. Suitable excipients are, for example, water, saline, dextrose, glycerol and the like. Of course, these compositions may also contain minor amounts of nontoxic, auxiliary substances such as wetting or emulsifying agents, pH buffering agents and so forth.

Systemic administration can also be implemented through implantation of a slow release or sustained release system, by suppository, or, if properly formulated, orally. Formulations for these modes of administration are well known in the art, and a summary of such methods may be found, for example, in *Remington's Pharmaceutical Sciences* (supra).

For diagnosis, the compounds may be used alone or may be labeled with a radioisotope or other detecting means.

If treatment is to be localized, such as for the treatment of superficial tumors or skin disorders, the active compounds may be topically administered using standard topical compositions involving lotions, suspension, or pastes.

The quantity of compounds to be administered depends on the choice of active ingredient, the condition to be treated, the mode of administration, the individual subject, and the judgment of the practitioner. Depending on the specificity of the preparation, smaller or larger doses may be needed. For compositions which are highly specific to target tissues, such as those which include a highly specific monoclonal immunoglobulin preparation or specific receptor ligand, dosages in the range of 0.05–1 mg/kg are suggested. For compositions which are less specific to the target tissue, larger doses, up to 1–10 mg/kg may be needed. The foregoing ranges are merely suggestive, as the number of variables in regard to an individual treatment regime is large and considerable excursions from these recommended values are expected.

The wavelength of irradiating light is chosen for specific application to correlate to the absorption spectrum of the photosensitizer and in many cases is close to the maximum absorbance of the photosensitizer. For most of the invention compounds, the preferable wavelength is between about 680 and 700 nm. The suitable wavelength for any of the photosensitizers can readily be determined from its absorption spectrum. Preferred irradiation dosages are in the range of 50–500 J cm$^{-2}$, and preferred irradiation dosage rates are in the range of 100–300 mW cm$^{-2}$.

In addition to in vivo use, the compounds of the invention can be used in the treatment of materials in vitro to destroy harmful viruses or infectious agents. For example, blood plasma or blood which is to be used for transfusion or banked for future transfusion can be treated with the compounds of the invention and irradiated to effect sterilization. In addition, biological products such as Factor VIII which are prepared from biological fluids can be irradiated in the presence of the compounds to destroy contaminants.

The following examples are intended to illustrate the invention, but not to limit its scope.

EXAMPLE 1

Preparation of the Mono- and Dimethylenyl Adduct of 1,3-Octaethylporphyrindione

To a solution of Ph$_3$PCH$_3$Br (630 mg, 1.76 mmol) in dry THF was added one equivalent of n-BuLi (1.6M solution in hexane) under argon. The resultant orange suspension was stirred at room temperature for 30 min before being added to a solution of 1,3-dione 2 (50 mg, 0.088 mmol) in 20 ml of THF at 0° C. The mixture was then allowed to warm to room temperature and stirred for 20 h. The reaction was quenched by addition of 10 ml of water and 100 ml of CH$_2$Cl$_2$. The organic layer was separated, washed three times with water and dried under reduced pressure. Separation on TLC plate, developed with CH$_2$Cl$_2$/hexane (2:3), gave four bands: the fastest moving green dimethylenyl compound 1-(1) (12 mg, 25%), followed by the brown-green 1-methylenyl compounds 1-(2) (12 mg, 24%), the gray-green 3-methylenyl component 1-(3) (16 mg, 33%) and the dark green starting material 2 (4.5 mg, 9%).

The structures of compounds 1-(1); 1-(2); and 1-(3) were verified by spectroscopy as follows:

1-(1): 1,3-dimethylenyl-2,2,4,4,5,6,7,8-octaethylisobacteriochlorin;

1-(2): 1-methylenyl-2,2,4,4,5,6,7,8-octaethyl-3-porphyrinone;

1-(3) 3-methylenyl-2,2,4,4,5,6,7,8-octaethyl-1-porphyrinone.

EXAMPLE 2

Preparation of The Dicyanomethylenyl Adducts

A.

1-(alpha,alpha-Dicyanomethylenyl)-2,2,3,4,5,6,7,8-octaethylchlorin

To a solution of Cu(II) porphyrinone 1 (50 mg, 0.082 mmol) in 50 ml of CHCl$_3$, titanium tetrachloride (32 mg. 0.16 mmol) was added and the suspension was brought to refluxing for 5 min under argon before a solution of malononitrile (54 mg, 0.82 mmol) and pyridine (150 mg, 1.9 mmol) in 15 ml of CHCl$_3$ was added. The mixed solution was continued to reflux for 30 min. To the cooled mixture, 50 ml of CHCl$_3$ was added and the solution was washed with water (3×50 ml) before being brought to dryness in vacuo. To remove the copper ion, the residue was dissolved in 10 ml of CF$_3$CO$_2$H, and H$_2$S gas was bubbled into the solution for 20 min. The acid solution was then diluted with 100 ml of chloroform and filtered on celite. The filtrate was washed with aqueous sodium acetate (25%, 2×50 ml), then water (3×50 ml), and evaporated to dryness. The crude product was chromatographed on TLC plate, developed with 1% HCO$_2$H/CH$_2$Cl$_2$, to give the light green-colored title compound (17 mg, 35%) and the purple-colored protonated porphyrinone 1-free base (23 mg, 51%).

B. 1,3-Bis-(alpha,alpha-dicyanomethylenyl)-2,2,4,4,5,6,7,8-octaethylisobacteriochlorin and 3-(alpha,alpha-dicyano methylenyl)-2,2,4,4,5,6,7,8-octaethyl-1-porphyrinone Cu(II) 11,3-OEPdione (50 mg, 0.08 mmol) in 50 ml of CHCl$_3$ was treated with TiCl$_4$ (64 mg, 0.32 mmol) and then reacted with 105 mg (1.6 mmol) of malonoitrile and 253 mg (3.2 mmol) of pyridine in 15 ml of CHCl$_3$. After refluxing for 30 min, the reaction mixture was allowed to cool, diluted with another 50 ml of CHCl$_3$, and washed with water (3×50 ml). Separation on TLC plate, with CH$_2$Cl$_2$ only, gave the unreacted starting material Cu(II) 2 (27.5 mg, 55%) as the fastest moving green band, followed by the green-brown dicyano Cu(II) monoadduct title compound, the orange-colored Cu(II) bis adduct title compound (7.5 mg, 13%) and a green-colored unknown compound.

The zinc complexes of mono and bis adducts were prepared from 50 mg of Zn(II) 1,3-OEPdione 2 in the same manner as described above. To remove the zinc ion, the crude product mixture was stirred in 10 ml of concentrated sulfuric acid for 2 h and then the acid solution was poured onto 100 g of ice with 10 g of sodium acetate. The precipitated crude product was collect by filtration on celite, washed with water and redissolved in methylene chloride. The solvent was evaporated and the residue was chromatographed on TLC plate (CH$_2$Cl$_2$). The fastest moving yellow-green component was identified as the dicyano mono adduct compound (19 mg, 39%), followed by the green band of starting material 2(11 mg, 24%) and the orange-colored compound bis adduct (15 mg, 28%).

C. 2-(alpha,alpha-Dicyanomethylenyl-1,1,4,4,5,6,7,8-octaethyl-3-porphyrinone and 2,3-Bis-(alpha,alpha-dicyanomethyl)1,1,4,4,5,6,7,8-octaethylisobacteriochlorin These compounds were prepared as in paragraph B. Separation on TLC plate gave three bands. The least polar was green-yellow band (24%) of the mono adduct followed by green unreacted 2,3-dione 3 (52%) and the yellow (16%) bis adduct.

D. 5-(alpha,alpha-Dicyanomethylenyl)-2,2,3,4,6,6,7,8-octaethyl-1-porphyrinone and 1,5-bis-(alpha,alpha-dicyano methylenyl)-2,2,3,4,6,6,7,8-octaethylbacteriochlorin The Cu(II) complex of the mono adduct title compound (32%) and bis adduct title compound (10%) were prepared as in paragraph B. Both complexes gave the similar brown-yellow color on TLC plate, developed with CH$_2$Cl$_2$, with the dicyano moving in front of the tetracyano compound. Treatment of the product mixture with H$_2$SO$_4$ gave the free base of the mono adduct only; the Cu(II) of the bis adduct remained intact.

EXAMPLE 3

Preparation of the N-Cyanoimine Adducts

A. 1-(N-Cyanoiminyl)-2,2,3,4,5,6,7,8-octaethylchlorin

To a solution of porphyrinone 1 (55 g, 0.1 mmol) in 100 ml of dry CH$_2$Cl$_2$ was added 0.4 ml of TiCl$_4$. The solution was stirred at room temperature for 5 min before being treated with a solution of bis-(trimethylsilyl)carbodiimide (56 mg, 0.3 mmol) in 10 ml of CH$_2$Cl$_2$. The reaction mixture was stirred at room temperature for 3 h under argon and filtered through celite. The filtrate was washed with 40 ml of aqueous NaOAc (25%) and then with water. The solvent was evaporated in vacuo and the residue was chromatographed on preparative TLC plate (silica gel CH$_2$Cl$_2$/hexane) to separate the slower moving green title compound (36 mg, 62%) from the brown starting material (19 mg, 34%).

B. 3-(N-Cyanoiminyl)-2,2,4,4,5,6,7,8-octaethyl-1-porphyrinone and 1,3-Bis-(N-cyanoiminyl)-2,2,4,4,5,6,7,8-octaethylisobacteriochlorin In the presence of 0.8 ml of TiCl$_4$, 1,3-OEPdione (56.6 mg, 0.1 mmol) and bis-(trimethylsilyl)-carbodiimide (112 mg, 0.8 mmol) were reacted as described for in paragraph A of this example. Separation on TLC plate gave the fast-moving dark green starting material (4 mg, 7%), followed by the light green mono adduct (18 mg, 32%) and the green bis adduct (34 mg, 55%).

C. 3-(N-Cyanoiminyl)-1,1,4,4,5,6,7,8-octaethyl-2-porphyrinone and 2,3-Bis-(N-cyanoiminyl)-1,1,4,4,5,6,7,8-octaethylisobacteriochlorin These compounds were prepared as in paragraph A of this example. Separation on TLC plate with HCO$_2$H/benzene gave mainly two bands, the faster-moving green mono adduct (54%) and the slower-moving yellow-green bis adduct (32%).

D. 5-(N-Cyanoiminyl)-2,2,3,4,6,6,7,8-octaethyl-1-porphyrinone and 1,5-Bis-(N-cyanoiminyl)-2,2,3,4,6,6,7,8-octaethylbacteriochlorin These compounds were prepared as in paragraph A of this example. Separation on TLC plate CH$_2$Cl$_2$/hexane gave three bands. The least polar blue-purple starting material 4 band (48%) was followed by green mono adduct (48%) and light green bis adduct (23%).

EXAMPLE 4

Preparation of the Thione Adducts

A. 2,2,3,4,6,6,7,8-Octaethyl-5-thio-1-porphyrindione and 2,2,3,4,6,6,7,8-Octaethyl-1,5-porphyrindithione Lawesson's reagent (240 mg, 0.6 mmol) was added to a boiling solution of 1,5-OEPdione 4 (56.6 mg, 0.1 mmol) in dry THF (100 ml) and the reaction mixture was refluxed under argon for 10 h. The solvent was evaporated in vacuo and the residue was chromatographed on preparative TLC plate (silica gel, CH$_2$Cl$_2$/hexane) to give the fast-moving brown-green dithione (14 mg, 23%) followed by the green monothione (20 mg, 35%) and the unreacted dione 4 (18 mg, 32%).

B. 2,2,3,4,5,5,7,8-Octaethyl-6-thio-1-porphyrindione and 2,2,3,4,5,5,7,8-Octaethyl-1,6-porphyrindithione These compounds were prepared as in paragraph A of this example. Separation on TLC plate gave mainly the green monothione (34%) together with a small amount of brown-green dithione (4%) and starting material (52%). Reaction of starting material once again with Lawesson's reagent brought about the formation of dithione in a yield of 63%.

In all of the foregoing examples, structures of the product title compounds were verified by suitable NMR, UV-visible, IR and MS spectra. The illustrated compounds are summarized in Table 1.

TABLE 1

| Example | Formula | =X | R |
|---------|---------|----|----|
| 1(1) | 2 | 1,3 =CH$_2$ | all Et |
| 1(2) | 2 | 1 =CH$_2$, 3 =O | all Et |
| 1(3) | 2 | 1 =O; 3 =CH$_2$ | all Et |
| 2-A | 1 | 1 =C(CN)$_2$ | all Et |
| 2-B(1) | 2 | 1,3 =C(CN)$_2$ | all Et |
| 2-B(2) | 2 | 1 =O; 3 =C(CN)$_2$ | all Et |
| 2-C(1) | 3 | 2 =C(CN)$_2$, 3 =O | all Et |
| 2-C(2) | 3 | 2,3 =C(CN)$_2$ | all Et |
| 2-D(1) | 4 | 1 =O, 5 =C(CN)$_2$ | all Et |
| 2-D(2) | 4 | 1,5 =C(CN)$_2$ | all Et |
| 3A | 1 | 1 =NCN | all Et |
| 3B(1) | 2 | 1 =O, 3 =NCN | all Et |
| 3B(2) | 2 | 1,3 =NCN | all Et |
| 3C(1) | 3 | 2 =O, 3 =NCN | all Et |
| 3C(2) | 3 | 1,3 =NCN | all Et |
| 3D(1) | 4 | 1 =O, 5 =NCN | all Et |
| 3D(2) | 4 | 1,5 =NCN | all Et |
| 4A(1) | 4 | 1 =O, 5 =S | all Et |
| 4A(2) | 4 | 1,5 =S | all Et |
| 4B(1) | 5 | 1 =O, 6 =S | all Et |
| 4B(2) | 5 | 1,6 =S | all Et |

We claim:

1. A compound of formulas 1-6 of FIG. 1,
   wherein each R is independently H, alkyl(1-6) or omega-carboxyalkyl(1-6) or the ester, amide or salt thereof, and
   wherein each =X is selected from the group consisting of =O, =S, =CR'$_2$, and NR",
   in which each R' is independently H, CN, alkyl(1-6), omega-carboxyalkyl(1-6) or the ester, amide or salt thereof, or aryl; and
   in which each R" is independently OH, CN, alkyl(1-6C) or omega-carboxyalkyl(1-6) or the ester, amide or salt thereof;
   with the proviso that all =X cannot be =O, and with the further proviso that if all =X are either =O or =S, all R cannot be ethyl.

2. The compound of claim 1 which is of formula 1.

3. The compound of claim 1 which is of formula 2 or 3 in which one =X is =O, and the other =X is selected from the group consisting of =S; =CR'$_2$; and NR".

4. The compound of claim 1 which is of formula 2 or 3 in which both =X are the same and are selected from the group consisting of =S; =CR'$_2$; and NR".

5. The compound of claim 1 which is of formula 4 or 5 in which one =X is =O and the other =X is selected from the group consisting of =S; =CR'$_2$; and NR".

6. The compound of claim 1 which is of formula 4 or 5 in which both =X are the same and are selected from the group consisting of =S; =CR'$_2$; and NR".

7. The compound of claim 1 which is of formula 6 wherein two =X are =O and the other is selected from the group consisting of =S; =CR'$_2$; and NR".

8. The compound of claim 1 which is of formula 6 wherein one =X is =O and the other two =X are identical and selected from the group consisting of =S; =CR'$_2$; and NR".

9. The compound of claim 1 which is of formula 6 wherein all =X are identical and selected from the group consisting of =S; =CR'$_2$; and NR".

10. A beta substituted porphyrin formed of four pyrrole rings wherein 1-3 of the carbons at positions 1-8 of said porphyrin are substituted with a substituent selected from the group consisting of =C(R')$_2$,=NR", and =S; with no more than one of the substituents in each of the pyrrole rings,
    wherein R' is selected from the group consisting of hydrogen, CN, lower alkyl (1-6C), aryl and omega-carboxy alkyl (1-6C) and the esters, amides and salts thereof, and
    wherein R" is selected from the group consisting of hydroxyl, CN, cyano and alkyl (1-6C), and omega-carboxy alkyl (1-6C) and the esters, amides and salts thereof, and
    with the proviso that when all said substituents are =S, the remaining substituents cannot all be ethyl,
    said beta substituted porphyrin having light absorption at greater than 680 nm.

* * * * *

UNITED STATES PATENT AND TRADEMARK OFFICE
CERTIFICATE OF CORRECTION

PATENT NO. : 5,064,952

DATED : 12 November 1991

INVENTOR(S) : Chang et al.

It is certified that error appears in the above-identified patent and that said Letters Patent is hereby corrected as shown below:

Column 1, line 5,
insert the following paragraph:

--This invention was made with government support under Research Grant #CA-42514, awarded by the National Institutes of Health. The government has certain rights in the invention.--

Signed and Sealed this

First Day of March, 1994

Attest:

*Attesting Officer*

BRUCE LEHMAN
*Commissioner of Patents and Trademarks*